United States Patent
Abt et al.

(10) Patent No.: US 11,253,275 B2
(45) Date of Patent: Feb. 22, 2022

(54) SURGICAL APPARATUS FOR CUTTING A TIBIA OF A PATIENT FOR THE IMPLANTATION OF AN ANKLE PROSTHESIS

(71) Applicants: FOURNITURES HOSPITALIERES INDUSTRIE, Quimper (FR); FH ORTHOPEDICS, Heimsbrunn (FR); AIC DEVELOPMENT GbR, Oberursel (DE)

(72) Inventors: Hans-Peter Abt, Oberursel (DE); Anna Impero, Sinnai (IT)

(73) Assignees: FOURNITURES HOSPITALIERES INDUSTRIE, Quimper (FR); AIC DEVELOPMENTGBR, Oberursel (DE); FH ORTHO, Heimsbrunn (FR)

(*) Notice: Subject to any disclaimer, the term of this patent is extended or adjusted under 35 U.S.C. 154(b) by 192 days.

(21) Appl. No.: 16/478,055

(22) PCT Filed: Jan. 5, 2018

(86) PCT No.: PCT/EP2018/050233
§ 371 (c)(1),
(2) Date: Jul. 15, 2019

(87) PCT Pub. No.: WO2018/130460
PCT Pub. Date: Jul. 19, 2018

(65) Prior Publication Data
US 2019/0365394 A1 Dec. 5, 2019

(30) Foreign Application Priority Data

Jan. 16, 2017 (IT) .................. 102017000001219

(51) Int. Cl.
*A61B 17/15* (2006.01)
*A61B 17/17* (2006.01)
*A61B 90/00* (2016.01)

(52) U.S. Cl.
CPC .......... *A61B 17/1775* (2016.11); *A61B 17/15* (2013.01); *A61B 90/08* (2016.02); *A61B 2090/0807* (2016.02)

(58) Field of Classification Search
CPC .... A61B 17/1775; A61B 17/14; A61B 17/142
See application file for complete search history.

(56) References Cited

U.S. PATENT DOCUMENTS

| 7,534,246 B2* | 5/2009 | Reiley ................. A61F 2/30771 606/96 |
| 7,717,920 B2* | 5/2010 | Reiley ................... A61B 17/72 606/96 |

(Continued)

FOREIGN PATENT DOCUMENTS

| EP | 2124832 A2 | 12/2009 |
| WO | 2008078082 A2 | 7/2008 |

(Continued)

OTHER PUBLICATIONS

International Search Report for Application No. PCT/EP2018/050233.
Written Opinion for Application No. PCT/EP2018/050233.

*Primary Examiner* — Zade Coley
(74) *Attorney, Agent, or Firm* — Cantor Colburn LLP

(57) ABSTRACT

The surgical apparatus comprising a support frame having an anterior portion configured to bear on an upper surface of a talus of the patient, and a rear portion configured to be secured to the tibia of the patient; and a cutting guide insert mounted on the support frame and configured to guide a cutting blade for cutting of a lower end part of the tibia.

18 Claims, 4 Drawing Sheets

(56) References Cited

U.S. PATENT DOCUMENTS

| | | | | |
|---|---|---|---|---|
| 2002/0055744 A1* | 5/2002 | Reiley | ............... | A61B 17/15 606/79 |
| 2006/0142870 A1* | 6/2006 | Robinson | ............ | A61B 17/142 623/21.18 |
| 2006/0229730 A1* | 10/2006 | Railey | ............ | A61B 17/1775 623/21.18 |
| 2010/0100097 A1* | 4/2010 | Wong | ............ | A61F 2/4644 606/79 |
| 2010/0262150 A1* | 10/2010 | Lian | ............ | A61F 2/4202 606/87 |
| 2012/0109131 A1* | 5/2012 | Vasarhelyi | ............ | A61B 17/16 606/79 |
| 2012/0130376 A1* | 5/2012 | Loring | ............ | A61B 17/025 606/80 |
| 2014/0031827 A1* | 1/2014 | Lancianese | ............ | A61F 2/4202 606/87 |
| 2015/0057665 A1* | 2/2015 | Neal | ............ | A61B 17/1739 606/87 |
| 2016/0128701 A1* | 5/2016 | Neal | ............ | A61B 17/1739 606/87 |
| 2016/0361071 A1* | 12/2016 | Mahfouz | ............ | A61B 17/1682 |

FOREIGN PATENT DOCUMENTS

| | | | |
|---|---|---|---|
| WO | 2013169475 A1 | 11/2013 | |
| WO | 2014020561 A1 | 2/2014 | |

\* cited by examiner

SURGICAL APPARATUS FOR CUTTING A TIBIA OF A PATIENT FOR THE IMPLANTATION OF AN ANKLE PROSTHESIS

CROSS REFERENCE TO RELATED APPLICATIONS

This application is a National Stage of PCT Application No. PCT/EP2018/050233 filed on Jan. 5, 2018, which claims priority to Italian Patent Application No. 102017000001219 filed on Jan. 16, 2017, the contents each of which are incorporated herein by reference thereto.

TECHNICAL FIELD

The present invention relates to a surgical apparatus for cutting a tibia of a patient for the implantation of an ankle prosthesis

BACKGROUND

As well known, the implantation of an ankle prosthesis takes place, in accordance with the patient's anatomy, through a sequence of cuts made with dedicated instruments.

In order to obtain a satisfactory implantation of an ankle prosthesis, it is required that the various cuts made on the various bones of the ankle joint are made accurately. Indeed, the mechanical strength of bone-prosthesis assembly depends precisely on the accuracy of the bone cuts made notably on the tibia and on the geometry of said cuts which should resemble to the geometry of the respective articular surfaces.

Therefore, a good primary stabilization of an ankle prosthesis and a complete ankle joint recovery require proper and precise bone cuts.

Currently, to adjust the various cutting parameters for the implantation of an ankle prosthesis, there are only external tibial cutting guides, which are difficult to position, which require many external adjustments, and which do not allow to perform accurately and precisely the complex sequence of required steps.

BRIEF SUMMARY

It is an object of the present invention to provide an improved surgical apparatus which can overcome the drawbacks encountered in conventional surgical apparatuses.

Another object of the present invention is to provide a surgical apparatus which simplifies the surgical technique and minimizes the number of external adjustments (which are the source of errors) needed to make the surgical cuts, and for example reduces said external adjustments to only one, in order to improve the cutting performance and to ensure a correct position of the tibial prosthesis component of an ankle prosthesis.

In other words, a purpose of the present invention is to provide a surgeon with an accurate instrument to perform easily and quickly the cuts that precede the implantation of ankle prosthesis.

According to the invention such a surgical apparatus for cutting a tibia of a patient for the implantation of an ankle prosthesis, the surgical apparatus comprising:

a support frame having an anterior portion configured to bear on an upper surface of a talus of the patient, and a rear portion configured to be secured to the tibia of the patient;

a cutting guide insert mounted on the support frame and configured to guide a cutting blade for the cutting of a lower end part of the tibia.

Such a configuration of the surgical apparatus according to the present invention allows to eliminate a series of adjustment steps previously necessary for the positioning of the tibial cutting guides of the prior art, thus eliminating the inevitable inaccuracies sources due to said series of adjustment steps.

Further the configuration of the support frame, and particularly the presence of the anterior portion of the support frame, ensures an introduction of the anterior portion between the articular surfaces of the talus and of the tibia (i.e. an intra-articular introduction of the anterior portion) and thus an automatic and perfect alignment of anatomical landmarks notably of the talus and the tibia of the patient. Such an automatic alignment ensures a proper and easy positioning of the surgical apparatus with respect to the talus and the tibia of the patient and thus a proper cutting of the tibia which is perfectly adapted to the anatomy of the patient. Therefore the configuration of the present surgical apparatus results in an improvement of the subsequent implantation of the ankle prosthesis.

Consequently, the present invention ensures correct positioning and alignment of a cutting guide insert to the anatomy of an ankle joint, and therefore a reliable and accurate subsequent implantation of an ankle prosthesis.

The present invention allows also to execute, with a single apparatus, sequence of adjustments and steps which are generally required for proper implantation of an ankle prosthesis (alignment to the tibial axis, localization of the tibial roof, adjustment of the tibial slope, localization and regulation of rotation of the distal part of the tibia, proper alignment lateral/medial, choosing the right size of the cutting guide).

Furthermore, the geometry of the surgical apparatus reduces the effect of "push-out" of the ankle prosthesis and provides a large mechanical stability within the articulation.

The surgical apparatus may also include one or more of the following features, taken alone or in combination.

According to an embodiment of the invention, the rear portion of the support frame is configured to be secured to a front surface of the tibia. Such a configuration of the support frame allows to operate the patient according to a frontal (and non-lateral) approach. Such a frontal approach allows to remove and subsequently rebuild bone portions not directly affected by the intervention.

According to an embodiment of the invention, the anterior portion of the support frame is configured to bear on a tibial articular surface of the talus of the patient.

According to an embodiment of the invention, the anterior portion is also configured to be supported by the talus.

According to an embodiment of the invention, the cutting guide insert is configured to guide the cutting blade along a main trajectory.

According to an embodiment of the invention, the main trajectory is transversal, and for example substantially orthogonal, to a longitudinal axis of the tibia when the rear portion of the support frame is secured to the tibia.

According to an embodiment of the invention, the cutting guide insert is movably mounted on the rear portion of the support frame along a displacement direction so as to adjust a tibial cutting height. Such a configuration of the surgical apparatus ensures a cut of the lower end part of the tibia which is more accurate, and thus an implantation of an ankle prosthesis which is more accurate and more reliable.

According to an embodiment of the invention, the displacement direction extends substantially parallely to a longitudinal axis of the tibia when the rear portion of the support frame is secured to the tibia.

According to an embodiment of the invention, the surgical apparatus further includes graduations provided on the support frame or on the cutting guide insert, each graduation corresponding to a value of the tibial cutting height; and a reading mark associated with the graduations and provided on the cutting guide insert or on support frame.

According to an embodiment of the invention, the support frame includes at least one immobilization member configured to immobilize the cutting guide insert on the support frame.

According to an embodiment of the invention, the at least one immobilization member is a pressure screw.

According to an embodiment of the invention, the support frame includes at least one elongated opening in which is slidably mounted the at least one immobilization member, the at least one elongated opening extending substantially parallely to the displacement direction.

According to an embodiment of the invention, the cutting guide insert includes at least one hole configured to partially receive an end portion of the at least one immobilization member.

According to an embodiment of the invention, the at least one hole may be elongated.

According to an embodiment of the invention, the at least one immobilization member is movable between at least a first configuration in which the cutting guide insert is displaceable with respect to the support frame along the displacement direction in order to adjust the tibial cutting height, and a second configuration in which the at least one immobilization member immobilizes the cutting guide insert with respect to the support frame in order to keep the adjusted tibial cutting height.

According to an embodiment of the invention, the support frame comprises a main body forming the rear portion, and a tongue forming the anterior portion.

According to an embodiment of the invention, wherein the tongue includes a lower concave surface configured to bear on the upper surface of the talus, and an upper convex surface configured to cooperate with a lower end of the tibia. Said configuration of the tongue allows an optimal positioning of the tongue between the talus and the tibia of a patient, and thus ensures an optimal adaptation of the surgical apparatus to the profile of the ankle joint. Further, due to the specific shape of the tongue, the support frame automatically orients to the anatomy of the tibia when the tongue is positioned on the upper face of the talus. Such an automatic orientation allows to perform the tibial cut more easily and reliably, without any manual adjustments or alignments that are often incorrect.

According to an embodiment of the invention, the tongue is curved.

According to an embodiment of the invention, the lower concave surface is curved and the upper convex surface is curved.

According to an embodiment of the invention, the lower concave surface of the tongue is at least partially complementary to the upper surface of the talus, and for example to the tibial articular surface, and the upper convex surface of the tongue is at least partially complementary to the lower end of the tibia, and for example to the tibial roof.

According to an embodiment of the invention, the tongue has substantially a saddle shape.

According to an embodiment of the invention, an end part of the tongue has a thickness of about 1 mm.

According to an embodiment of the invention, the main body has a substantially prismatic shape.

According to an embodiment of the invention, the main body of the support frame includes a housing in which the cutting guide insert is inserted.

According to an embodiment of the invention, the housing is an upwardly open housing.

According to an embodiment of the invention, the main body of the support frame further comprises a curved front surface configured to substantially face a front surface of the tibia when the rear portion is secured to the tibia.

According to an embodiment of the invention, the support frame includes a first immobilization member and a second immobilization member configured to immobilize the cutting guide insert on the support frame, the first immobilization member being provided on a side wall of the main body and the second immobilization member being provided on a rear wall of the main body.

According to an embodiment of the invention, the support frame includes a first elongated opening provided on the side wall of the main body and in which is slidably mounted the first immobilization member, and a second elongated opening provided on the rear wall of the main body and in which is slidably mounted the second immobilization member.

According to an embodiment of the invention, the curved front surface of the main body is configured to bear on the front surface of the tibia when the rear portion is secured to the tibia.

According to an embodiment of the invention, the surgical apparatus further includes at least one bone anchoring member configured to be anchored to the tibia and to secure the rear portion of the support frame to the tibia of the patient.

According to an embodiment of the invention, the at least one bone anchoring member is provided on the main body.

According to an embodiment of the invention, the surgical apparatus includes two bone anchoring members. Advantageously, the bone anchoring members converge forwardly.

According to an embodiment of the invention, the at least one bone anchoring member is a bone anchoring pin.

According to an embodiment of the invention, the main body of the support frame further includes connecting elements configured to accommodate removable coupling means.

According to an embodiment of the invention, the cutting guide insert has at least one guiding groove configured to guide the cutting blade.

According to an embodiment of the invention, the at least one guiding groove defines a curved guiding surface.

According to an embodiment of the invention, the at least one guiding groove defines a straight guiding surface.

According to an embodiment of the invention, the at least one guiding groove defines at least in part the main trajectory.

According to an embodiment of the invention, the cutting blade is adapted to be inserted in the at least one guiding groove to follow the main trajectory.

According to an embodiment of the invention, the at least one guiding groove includes a tibial guiding groove configured to guide the cutting blade for cutting the lower end part of the tibia, and a talus guiding groove configured to guide the cutting blade for cutting an upper end part of the talus.

According to an embodiment of the invention, the support frame and the cutting guide insert are made in stainless steel.

The present invention also relates to a surgical system including at least one surgical apparatus according to the invention, and at least one cutting blade having a determined curvature and configured to cut a lower end part of the tibia.

According to an embodiment of the invention, the at least one cutting blade has a determined curvature. However, according to another embodiment of the invention, the at least one cutting blade may be substantially planar and may be configured to perform a straight cut on the lower end part of the tibia.

According to an embodiment of the invention, the at least one cutting blade may also be configured to cut an upper end part of the talus.

According to an embodiment of the invention, the surgical system may include cutting blades having different sizes, and cutting guide inserts having different sizes, each size of the cutting blade and of the cutting guide insert corresponding to a size of a respective tibial prosthetic component.

According to an embodiment of the invention, the surgical system may include several support frames comprising anterior portions having different thicknesses. Thus, if, after having positioning an anterior portion of a selected support frame between the talus and the tibia of a patient, there is an excessive clearance between the anterior portion and the bones of the ankle of the patient, the surgeon may replace the previously selected support frame with a support frame comprising an anterior portion having a higher thickness in order to limit or cancel said clearance.

BRIEF DESCRIPTION OF THE DRAWINGS

These and other advantages will become apparent upon reading the following description in view of the drawing attached hereto representing, as non-limiting example, one embodiment of a surgical apparatus according to the invention.

The following detailed description of two embodiments of the invention is better understood when read in conjunction with the appended drawings being understood, however, that the invention is not limited to the specific embodiments disclosed.

FIGS. 1 to 7 represent a surgical apparatus 2 for cutting a tibia of a patient for the implantation of an ankle prosthesis.

DETAILED DESCRIPTION

Figure 7:
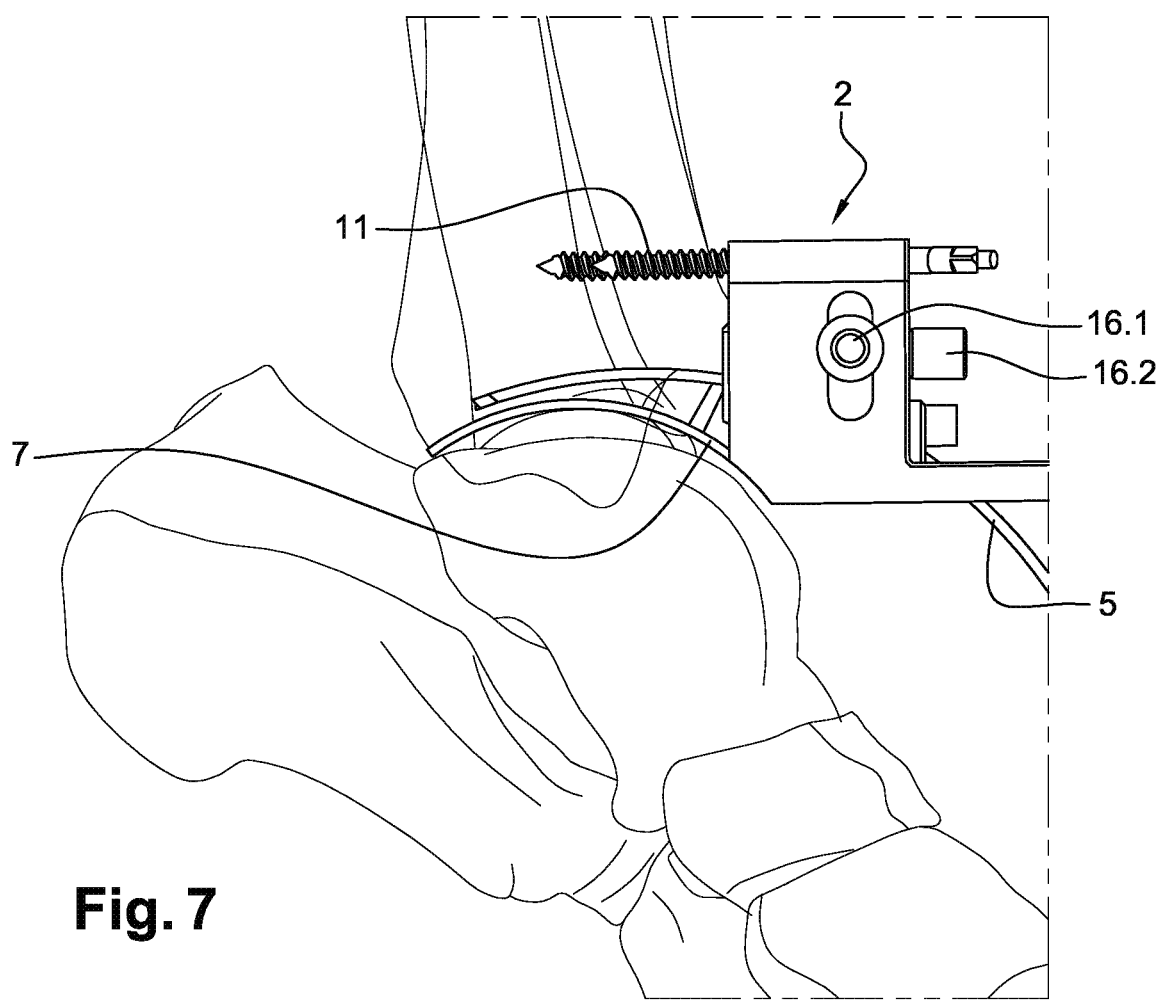
FIG. 7 is a schematic view of the surgical apparatus of FIG. 1 secured to a tibia.

The surgical apparatus 2 comprises a support frame 3 configured to be secured to the tibia of the patient, and a cutting guide insert 4 movably mounted on the support frame 3 and configured to guide a cutting blade 5 (see FIG. 7) for cutting of a lower end part of the tibia. The support frame 3 and the cutting guide insert 4 may for example be made in stainless steel, and the cutting blade 5 has advantageously a determined curvature.

Figure 1:
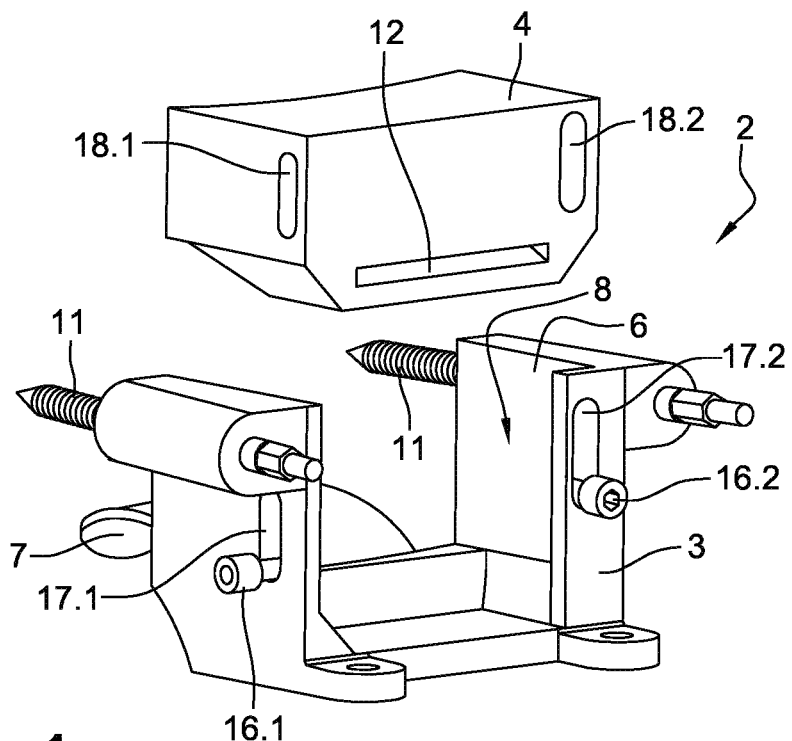
FIG. 1 is an exploded perspective view of a surgical apparatus according to a first embodiment of the present invention.
Figure 2:
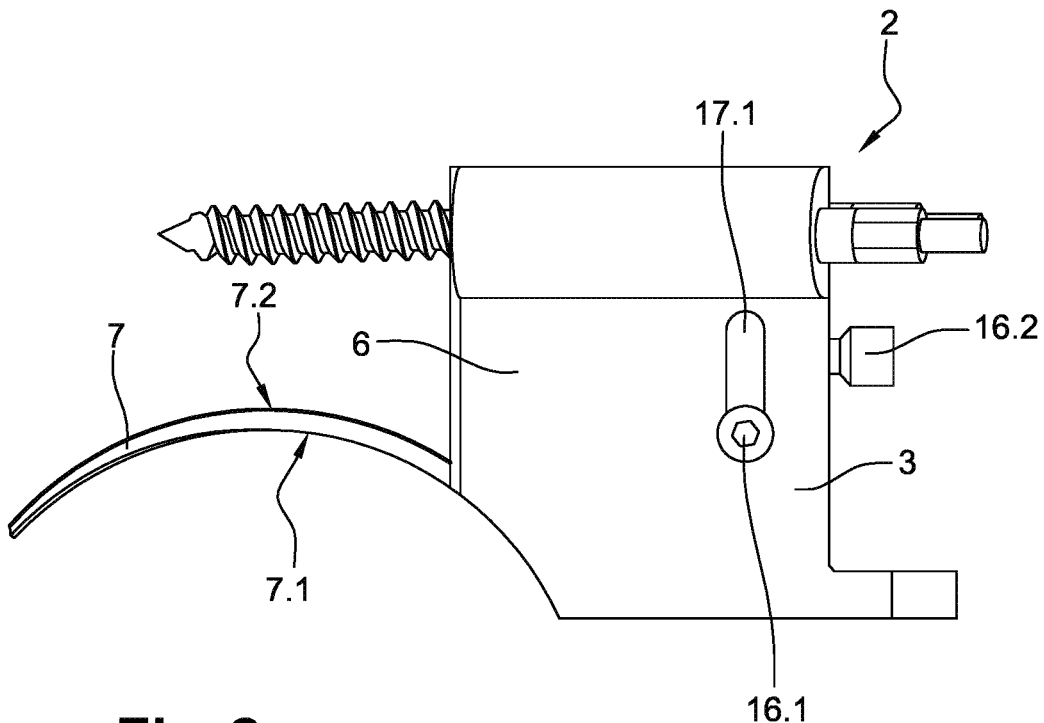
FIG. 2 is a side view of the surgical apparatus of FIG. 1.
Figure 3:
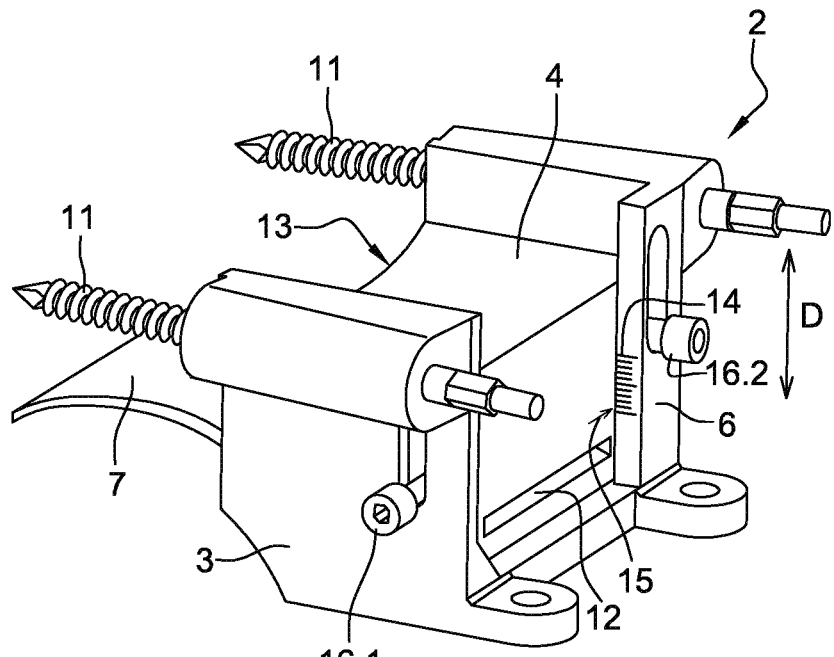
FIG. 3 is a perspective view of the surgical apparatus of FIG. 1.
Figure 4:
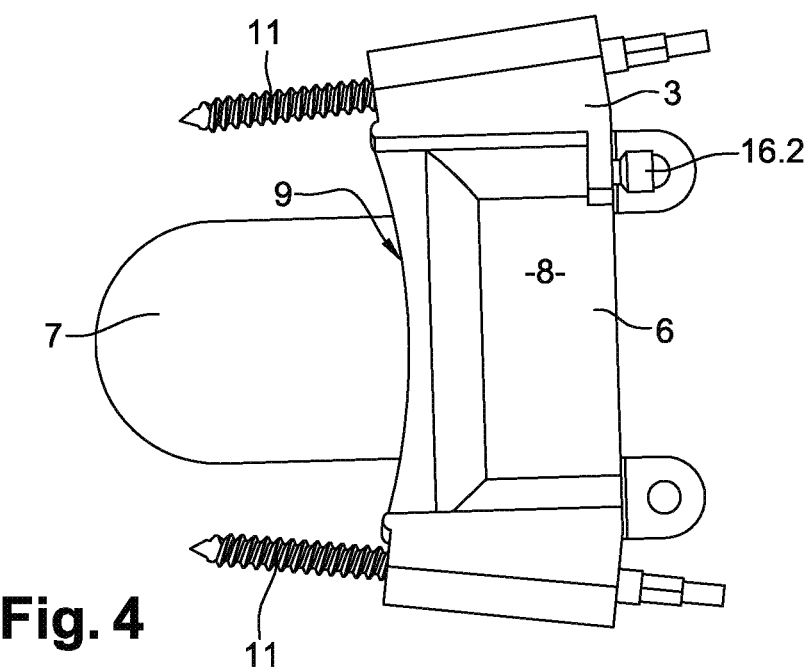
FIG. 4 is a top view of a support frame of the surgical apparatus of FIG. 1.
Figure 5:
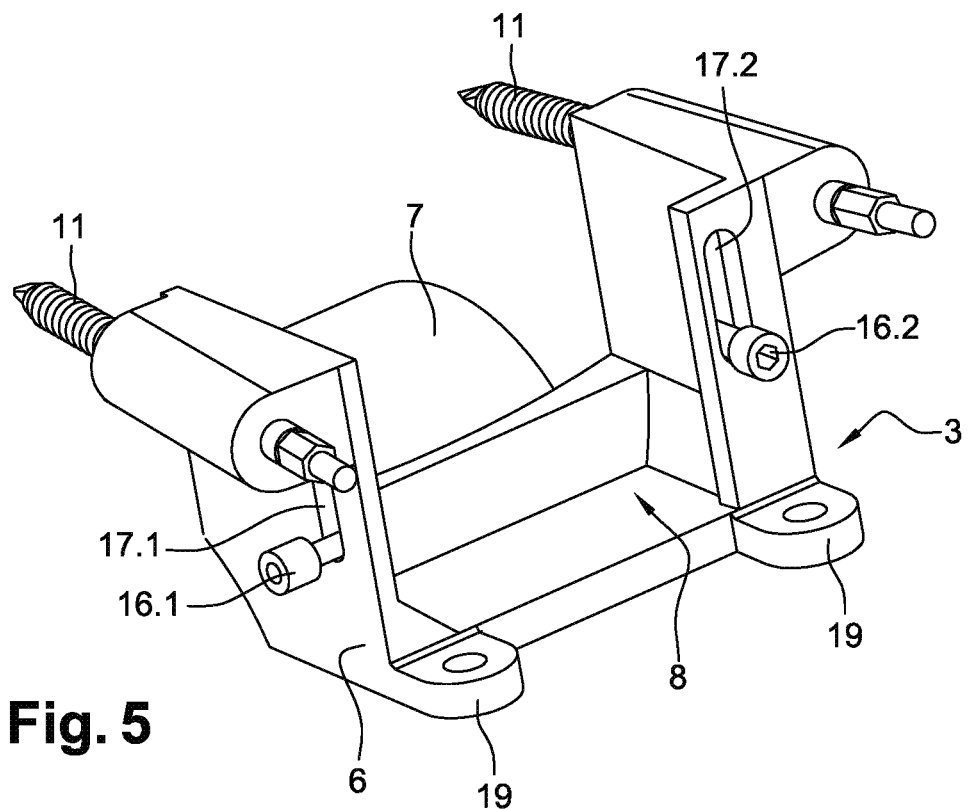
FIG. 5 is a perspective view of the support frame of FIG. 4.

As better shown on FIGS. 4 and 5, the support frame 3 includes a main body 6 forming a rear portion of the support frame 3 an configured to be secured to a front surface of the tibia of the patient, and a tongue 7 forming an anterior portion of the support frame 3 and configured to bear on a tibial articular surface of a talus and to be supported by the tibial articular surface.

The tongue 7 is curved and has substantially a saddle shape. The tongue 7 particularly includes a lower concave surface 7.1 which is curved and configured to bear on the tibial articular surface of the talus, and an upper convex surface 7.2 which is curved and configured to cooperate with a lower end of the tibia. Advantageously, the lower concave surface 7.1 of the tongue 7 is at least partially complementary to the tibial articular surface of a talus, and the upper convex surface 7.2 of the tongue 7 is at least partially complementary to the lower end of a tibia, and for example to the tibial roof. The tongue 7 may include an end part having for example a thickness of about 1 mm.

The main body 6 includes an upwardly open housing 8 in which the cutting guide insert 4 is inserted. Further, as shown on FIG. 4, the main body 6 comprises a curved front surface 9 configured to substantially face a front surface of the tibia and to bear against said front surface of the tibia when the main body 6 is secured to the tibia. The main body 6 may for example have a substantially prismatic shape.

The surgical apparatus 2 further includes one or several bone anchoring member(s) 11 configured to be anchored to a tibia and to secure the main body 6 to the tibia. According to the embodiment shown on the figures, the surgical apparatus 2 includes two bone anchoring members 11 provided on the main body 6, for example on opposite side walls of the main body 6. The two bone anchoring members 11 may for example extend in a same plane and converge forwardly. Advantageously, each bone anchoring member 11 is a bone anchoring pin.

Figure 6:
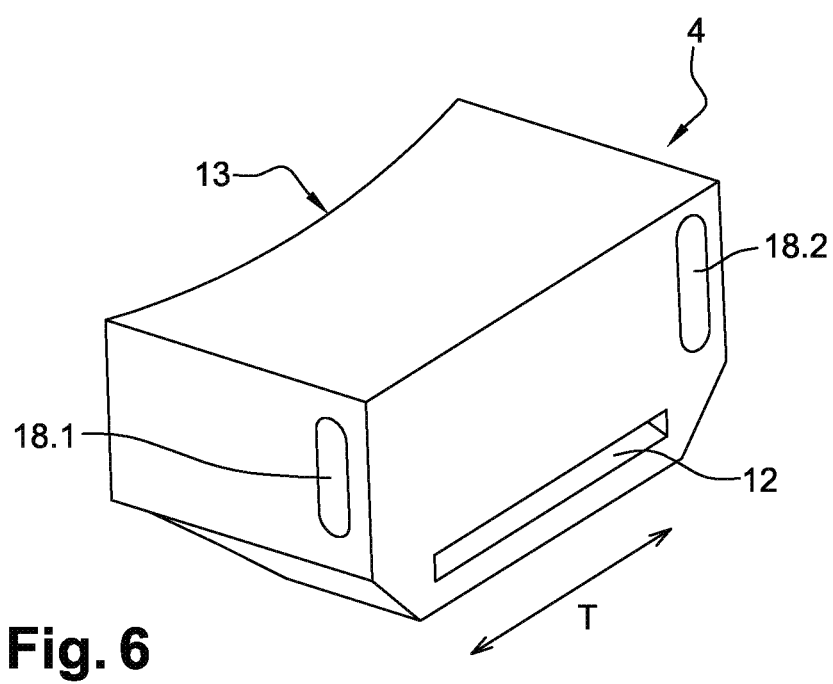
FIG. 6 is a perspective view of a cutting guide insert of the surgical apparatus of FIG. 1.

As better shown on FIG. 6, the cutting guide insert 4 includes a guiding groove 12 configured to guide the cutting blade 5 along a main trajectory T so as to cut of a lower end part of the tibia The main trajectory T is advantageously substantially orthogonal to a longitudinal axis of the tibia when the main body 6 of the support frame 3 is secured to the tibia.

Advantageously, the guiding groove 12 includes a curved guiding surface and defines the main trajectory T. The cutting blade 5 is particularly adapted to be inserted in the guiding groove 12 to follow the main trajectory T.

As the main body 6, the cutting guide insert 4 also includes a curved front surface 13 configured to substantially face the front surface of a tibia when the main body 6 is secured to the tibia and when the cutting guide insert 4 is inserted in the housing 8.

The cutting guide insert 4 is movably mounted on the main body 6 along a displacement direction D so as to adjust a tibial cutting height. The displacement direction D extends substantially parallely to a longitudinal axis of a tibia when the rear portion of the support frame 3 is secured to the tibia.

According to the embodiment shown on the figures, the surgical apparatus 2 includes graduations 14 provided on the support frame 3, and for example on the main body 6, each graduation corresponding to a value of the tibial cutting height, and a reading mark 15 associated with the graduations 14 and provided on the cutting guide insert 4. However, the graduations 14 may also be provided on the cutting guide insert 4 and the reading mark 15 may also be provided on the support frame 3.

Further, the support frame 3 includes one or several immobilization member(s) 16 configured to immobilize the cutting guide insert 4 on the main body 6. According to the embodiment shown on the figures, the support frame 3 includes a first immobilization member 16.1 provided on a side wall of the main body 6 and configured to immobilize the cutting guide insert 4 on the support frame 3, and a second immobilization member 16.2 provided on a rear wall of the main body 6 and also configured to immobilize the cutting guide insert 4 on the support frame 3. Each of the first and second immobilization members 16.1, 16.2 may be for example a pressure screw.

According to the embodiment shown on the figures, the main body 6 includes a first elongated opening 17.1 provided on the side wall of the main body 6 and in which is slidably mounted the first immobilization member 16.1, and a second elongated opening 17.2 provided on the rear wall of the main body 6 and in which is slidably mounted the second immobilization member 16.2. Each of the first and second elongated openings 17.1, 17.2 extends advantageously substantially parallely to the displacement direction D.

According to the embodiment shown on the figures, the cutting guide insert 4 further includes a first hole 18.1 provided on a side wall of the cutting guide insert 4 and configured to partially receive an end portion of the first immobilization member 16.1, and a second hole 18.2 provided on a rear wall of the cutting guide insert 4 and configured to partially receive an end portion of the second immobilization member 16.2. Each of the first and second holes 18.1, 18.2 may for example be elongated.

Advantageously, each of the first and second immobilization members 16.1, 16.2 is movable between a first configuration in which the cutting guide insert 4 is displaceable with respect to the support frame 3 along the displacement direction D in order to adjust the tibial cutting height, and a second configuration in which said immobilization member is partially received in the respective hole provided on the cutting guide insert 4 and immobilizes the cutting guide insert 4 with respect to the support frame 3 in order to keep the adjusted tibial cutting height.

As shown on FIG. 5, the main body 6 of the support frame 3 may also include connecting elements 19 configured to accommodate removable coupling means provided for example on a support device.

According to an embodiment of the invention, the cutting blade 5 may be provided in different sizes, and the cutting guide insert 4 may also be provided in different sizes, each size of the cutting blade 5 and of the cutting guide insert 4 corresponding to a size of a respective tibial prosthetic component.

According to another embodiment of the invention, the support frame 3 may also be provided in different sizes, and the several support frames 3 advantageously comprise tongues 7 having different thicknesses. Thus, if, after having positioning a tongue 7 of a selected support frame 3 between the talus and the tibia of a patient, there is an excessive clearance between the tongue 7 and the bones of the ankle of the patient, the surgeon may replace the previously selected support frame 3 with another support frame 3 comprising a tongue 7 having a higher thickness in order to limit or cancel said clearance.

Figure 8:
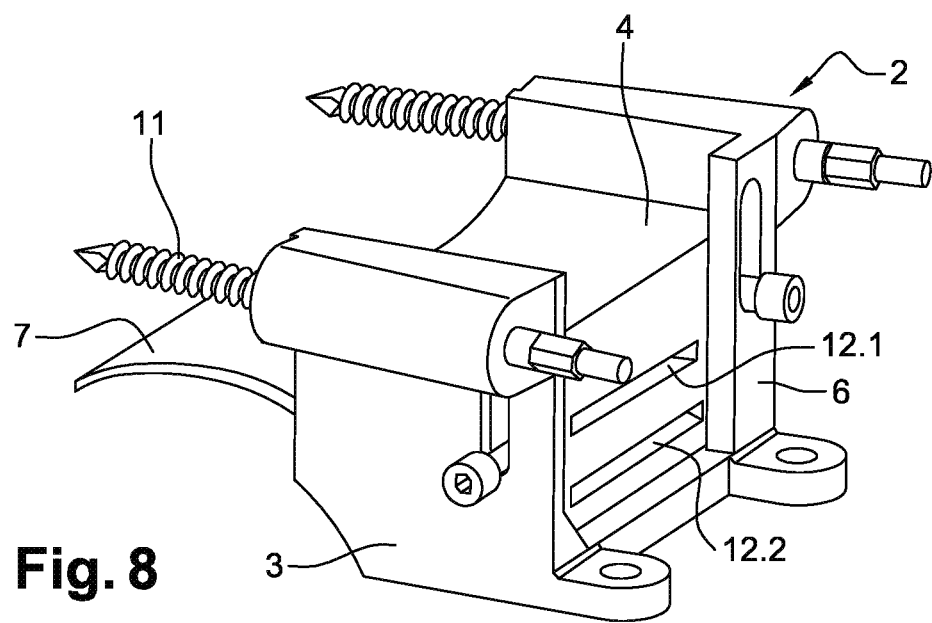
FIG. 8 is a perspective view of a surgical apparatus according to a second embodiment of the invention, secured to a tibia.

FIG. 8 disclose a surgical apparatus 2 according to a second embodiment of the invention which differs from the first embodiment substantially in that the cutting guide insert 4 includes two guiding grooves, and particularly a tibial guiding groove 12.1 configured to guide the cutting blade 5 for cutting a lower end part of the tibia of a patient, and a talus guiding groove 12.2 configured to guide the cutting blade 5 for cutting an upper end part of the talus of a patient.

Each of the tibial guiding groove 12.1 and the talus guiding groove 12.2 may have a determined curvature in order to guide a curved cutting blade 5 and to perform curved cuts on the talus and the tibia. However, each of the tibial guiding groove 12.1 and the talus guiding groove 12.2 may be straight in order to guide a straight cutting blade 5 and to perform straight cuts on the talus and the tibia. Advantageously, the tibial guiding groove 12.1 and the talus guiding groove 12.2 extend substantially parallel to each other.

Of course, the invention is not restricted to the embodiments described above by way of non-limiting examples, but on the contrary it encompasses all embodiments thereof.

The invention claimed is:

1. A surgical apparatus for cutting a tibia of a patient for implantation of an ankle prosthesis, the surgical apparatus comprising:
   a support frame having an anterior portion configured to bear on an upper surface of a talus of the patient, and a rear portion configured to be secured to the tibia of the patient, wherein the support frame comprises a main body forming the rear portion, and a tongue forming the anterior portion; and
   a cutting guide insert mounted on the support frame and configured to guide a cutting blade for cutting of a lower end part of the tibia, wherein the tongue includes a lower concave surface configured to bear on the upper surface of the talus, and an upper convex surface configured to cooperate with a lower end of the tibia.

2. The surgical apparatus according to claim 1, wherein the cutting guide insert is configured to guide the cutting blade along a main trajectory.

3. The surgical apparatus according to claim 2, wherein the main trajectory is transverse to a longitudinal axis of the tibia when the rear portion of the support frame is secured to the tibia.

4. The surgical apparatus according to claim 3, wherein the cutting guide insert is movably mounted on the rear portion of the support frame along a displacement direction so as to adjust a tibial cutting height.

5. The surgical apparatus according to claim 2, wherein the cutting guide insert is movably mounted on the rear portion of the support frame along a displacement direction so as to adjust a tibial cutting height.

6. The surgical apparatus according to claim 5, wherein the displacement direction extends substantially parallel to a longitudinal axis of the tibia when the rear portion of the support frame is secured to the tibia.

7. The surgical apparatus according to claim 1, wherein the cutting guide insert is movably mounted on the rear portion of the support frame along a displacement direction so as to adjust a tibial cutting height.

8. The surgical apparatus according to claim 7, wherein the displacement direction extends substantially parallel to a longitudinal axis of the tibia when the rear portion of the support frame is secured to the tibia.

9. The surgical apparatus according to claim 7, further including:

graduations provided on the support frame or on the cutting guide insert, each graduation corresponding to a value of the tibial cutting height; and a reading mark associated with the graduations and provided on the cutting guide insert or on support frame.

10. The surgical apparatus according to claim 7, wherein the support frame includes at least one immobilization member configured to immobilize the cutting guide insert on the support frame.

11. The surgical apparatus according to claim 10, wherein the at least one immobilization member is movable between at least a first configuration in which the cutting guide insert is displaceable with respect to the support frame along the displacement direction in order to adjust the tibial cutting height, and a second configuration in which the at least one immobilization member immobilizes the cutting guide insert with respect to the support frame in order to keep an adjusted tibial cutting height.

12. The surgical apparatus according to claim 1, wherein the main body of the support frame includes a housing in which the cutting guide insert is inserted.

13. The surgical apparatus according to claim 1, wherein the main body of the support frame further comprises a curved front surface configured to substantially face a front surface of the tibia when the rear portion is secured to the tibia.

14. The surgical apparatus according to claim 1, wherein the support frame includes a first immobilization member and a second immobilization member configured to immobilize the cutting guide insert on the support frame, the first immobilization member being provided on a side wall of the main body and the second immobilization member being provided on a rear wall of the main body, wherein the cutting guide insert is movably mounted on the rear portion of the support frame along a displacement direction so as to adjust a tibial cutting height.

15. The surgical apparatus according to claim 1, further including at least one bone anchoring member configured to be anchored to the tibia and to secure the rear portion of the support frame to the tibia of the patient.

16. The surgical apparatus according to claim 1, wherein the cutting guide insert has at least one guiding groove configured to guide the cutting blade.

17. The surgical apparatus according to claim 16, wherein the at least one guiding groove defines a curved guiding surface.

18. A surgical system including at least one surgical apparatus according to claim 1, and at least one cutting blade configured to cut a lower end part of the tibia.

* * * * *